US011134937B2

(12) United States Patent
Miraki

(10) Patent No.: US 11,134,937 B2
(45) Date of Patent: Oct. 5, 2021

(54) SUTURE CLIP

(71) Applicant: Edwards Lifesciences Corporation, Irvine, CA (US)

(72) Inventor: Manouchehr A. Miraki, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 203 days.

(21) Appl. No.: 16/455,164

(22) Filed: Jun. 27, 2019

(65) Prior Publication Data
US 2020/0000458 A1    Jan. 2, 2020

Related U.S. Application Data

(60) Provisional application No. 62/693,272, filed on Jul. 2, 2018.

(51) Int. Cl.
*A61B 17/04* (2006.01)
*A61B 17/122* (2006.01)
*A61B 17/128* (2006.01)

(52) U.S. Cl.
CPC ...... *A61B 17/0487* (2013.01); *A61B 17/0469* (2013.01); *A61B 17/122* (2013.01); *A61B 17/1285* (2013.01); *A61B 2017/0488* (2013.01)

(58) Field of Classification Search
CPC ... A61B 17/04; A61B 17/0401; A61B 17/122; A61B 17/08; A61B 17/083; A61B 17/0487; A61B 17/0469; A61B 17/1285; A61B 2017/0488; A61B 2017/04909; A61B 2017/0414

See application file for complete search history.

(56) References Cited

U.S. PATENT DOCUMENTS

| 5,634,584 A | 6/1997 | Okorocha et al. |
| 6,015,428 A | 1/2000 | Pagedas |
| 6,626,930 B1 | 9/2003 | Allen et al. |
| 7,049,244 B2 | 5/2006 | Becker et al. |
| 7,083,628 B2 | 8/2006 | Bachman |
| 7,381,210 B2 | 6/2008 | Zarbatany et al. |

(Continued)

FOREIGN PATENT DOCUMENTS

| EP | 0755655 A2 | 1/1997 |
| EP | 0755656 A2 | 1/1997 |

(Continued)

*Primary Examiner* — Vi X Nguyen
(74) *Attorney, Agent, or Firm* — Klarquist Sparkman, LLP

(57) ABSTRACT

Disclosed suture clips include a generally disk-shaped body having an annular outer body, first and second tabs extending radially inwardly from opposing sides of the annular outer body, first and second slots passing through a thickness of the suture clip and separating the annular outer body from lateral sides of the first and second tabs, and the first and second slots include stepped portions configured to align the suture clip on a rail of a clip deployment device. The stepped slots create bracketing surfaces that interface with the rail on which the clips are mounted, such that the bracketing surfaces prevent or limit the freedom of the clips from tilting or shifting relative to the rail. The disclosed clips can also include rounded edges on engagement surfaces of the tabs to minimize particulate formation.

9 Claims, 5 Drawing Sheets

(56) References Cited

U.S. PATENT DOCUMENTS

| | | | |
|---|---|---|---|
| 9,017,347 B2 | 4/2015 | Oba et al. | |
| 2004/0204724 A1* | 10/2004 | Kissel | A61B 17/10 606/151 |
| 2005/0251209 A1 | 11/2005 | Saadat et al. | |
| 2006/0089571 A1 | 4/2006 | Gertner | |
| 2006/0265042 A1 | 11/2006 | Catanese et al. | |
| 2006/0276871 A1 | 12/2006 | Lamson et al. | |
| 2007/0005079 A1 | 1/2007 | Zarbatany et al. | |
| 2007/0049970 A1 | 3/2007 | Belef et al. | |
| 2008/0154286 A1 | 6/2008 | Abbott et al. | |
| 2009/0272783 A1 | 11/2009 | Crainich et al. | |
| 2012/0053599 A1 | 3/2012 | Shikhman et al. | |
| 2012/0165865 A1 | 6/2012 | Fujisaki et al. | |
| 2013/0158600 A1* | 6/2013 | Conklin | A61B 17/0483 606/232 |
| 2013/0165953 A1 | 6/2013 | Oba et al. | |
| 2014/0031864 A1 | 1/2014 | Jafari et al. | |
| 2015/0142021 A1 | 5/2015 | Smith et al. | |
| 2016/0183937 A1 | 6/2016 | Miraki et al. | |

FOREIGN PATENT DOCUMENTS

| | | | |
|---|---|---|---|
| EP | 1484023 | A1 | 12/2004 |
| EP | 2455001 | A2 | 5/2012 |
| EP | 2462876 | A2 | 6/2012 |
| WO | 0128455 | A1 | 4/2001 |

\* cited by examiner

SUTURE CLIP

CROSS-REFERENCE TO RELATED APPLICATIONS

This application claims the benefit of U.S. patent application Ser. No. 62/693,272, filed Jul. 2, 2018, the entire disclosure of which is incorporate by reference. The entire disclosure of U.S. patent application Ser. No. 14/757,938 (published as U.S. Patent Application Publication No. 2016/0183937 A1 on Jun. 30, 2016), which describes related suture clips and suture clip deployment devices and methods, is hereby incorporated by reference in its entirety for all purposes. This application is also related to U.S. patent application Ser. No. 14/868,741, filed Sep. 29, 2015; U.S. patent application Ser. No. 14/543,240, filed Nov. 17, 2014; U.S. Pat. No. 9,017,347; U.S. Pat. No. 9,498,202; U.S. patent application Ser. No. 14/307,694, filed Jun. 18, 2014; U.S. patent application Ser. No. 14/329,797, filed Jul. 11, 2014; U.S. patent application Ser. No. 14/965,323, filed Dec. 10, 2015; and U.S. patent application Ser. No. 14/658,575, filed Mar. 16, 2015; all which are incorporated by reference herein in their entireties for all purposes.

FIELD

This disclosure relates to suture clips and devices and methods for securing sutures using suture clips.

BACKGROUND

Sutures are used for a variety of surgical purposes, such as approximation of tissue and ligation of tissue. When placing sutures, the strand of suture material to be used typically has a needle affixed to one end which is passed (looped) through the tissue to be approximated or ligated, forming a stitch. The stitch is then tensioned appropriately, and the two free ends of the suture loop, the needle end and the non-needle end, are knotted to retain the desired tension in the stitch. Forming knots in suture during open surgery is a simple matter, though time-consuming, but forming knots in sutures during endoscopic surgery can require two surgeons to cooperate in a multi-step process which is performed with multiple instruments to pass the needle and suture back and forth to tie the suture knot.

Suture locking devices can eliminate the need to tie knots in order to speed up surgical procedures. Suture clips, retainers, or locks are used in place of suture knots to prevent passage of a suture end into and through tissue and to maintain the tension applied to the suture material during a suturing procedure.

When using a method that employs a clip to secure sutures, the clip can be delivered by advancing the clip along the suture lines to the area of interest, and then engaging the clip to the sutures such that the clip secures the sutures in place. With the clip thus secured, the excess sutures can be cut and removed from the patient. However, deployment of several suture clips during a procedure can be very time consuming, difficult to accomplish without error, and prone to inconsistent tensioning from one clip to the next.

Multi-suture clip deployment systems can be used for deploying several consecutive suture clips onto suture without having to stop to reload the device have been developed. Such devices can also ensure consistent tensioning of the sutures being secured. In some deployment device, the several suture clips are mounted along a common rail. Each clip can include an internal opening including two opposing tabs that flex open to allow the rail to be positioned through the opening, thereby allowing the suture clips to be mounted around the rail with the tabs forced apart. As each clip is deployed off of the rail and onto a suture, the tabs resiliently flex closed and pinch the suture, securing the suture from pulling back through the tissue.

However, the suture clips mounted on the rail can sometimes become mis-aligned on the rail, causing the suture clips to misfire when deployed from the rail. This can result in the deployment device jamming and/or result in the clip not properly securing the suture as intended.

SUMMARY

Disclosed herein are improved suture clips that include stepped slots that help orient the clip on a rail of a deployment device and maintain the suture clips in proper alignment while sliding along the rail during use, avoiding malfunctioning of the delivery device. The stepped slots create bracketing surfaces that interface with the surfaces of a rail on which the clips are mounted, such that the bracketing surfaces prevent or limit the freedom of the clips from tilting or rotating or shifting relative to the rail. Disclosed suture clips also include rounded, smooth suture engagement edges that reduce the risk of particulate matter coming loose from the clips and harming a patient. The disclosed suture clips make the suture securement process more reliable, safer, and faster.

An exemplary suture clip for securing one or more sutures comprises a generally disk-shaped body having an annular outer body, a first tab extending radially inwardly from a first side of the annular outer body, a second tab extending radially inwardly from a second, opposing side of the annular outer body, a first slot and a second slot passing through a thickness of the suture clip and separating the annular outer body from lateral sides of the first tab and second tab, and a suture engagement slot passing through a thickness of the suture clip between the first tab and the second tab and connecting the first and second slots, wherein the suture engagement slot are sized to receive and hold one or more sutures between the first and second tabs, and wherein the first and second slots comprise stepped portions configured to align the suture clip on a rail of a clip deployment device. The stepped portions can be located on opposite sides of the suture engagement slot, and the stepped portions can comprise two stepped portions in the first slot and two stepped portion in the second slot. The stepped portions can define steps that extend inwardly from the annular outer body, and the stepped portions can define indentations in lateral sides of the first and second tabs. The stepped portions can be spaced apart by a distance that corresponds to a width dimension of a rail of a clip deployment device on which the suture clip in configured to be mounted. The first and second slots can comprise straight portions extending between the stepped portions. The first and second tabs can be configured to resiliently deform to increase the size of the suture engagement slot to allow a rail of a suture clip deployment device to pass through the suture clip between the first and second tabs. In some embodiment, the first and second slots can terminate in enlarged circular portions located where the first and second tabs join with the annular outer body, such that the enlarged circular portions reduce stress concentrations when the first and second tabs resiliently deform relative to the annular outer body along hinge axes extending between the enlarged circular portions. In some embodiments, the opposing suture engagement surfaces of the two tabs comprise rounded edges that contact and slide along the rail. In some embodiments, the rail comprises a coating or lubricant that reduces friction between the rail and the suture clip.

A further understanding of the features and advantages of the disclosed technology will become apparent from a consideration of the following detailed description.

DETAILED DESCRIPTION

Figure 1:
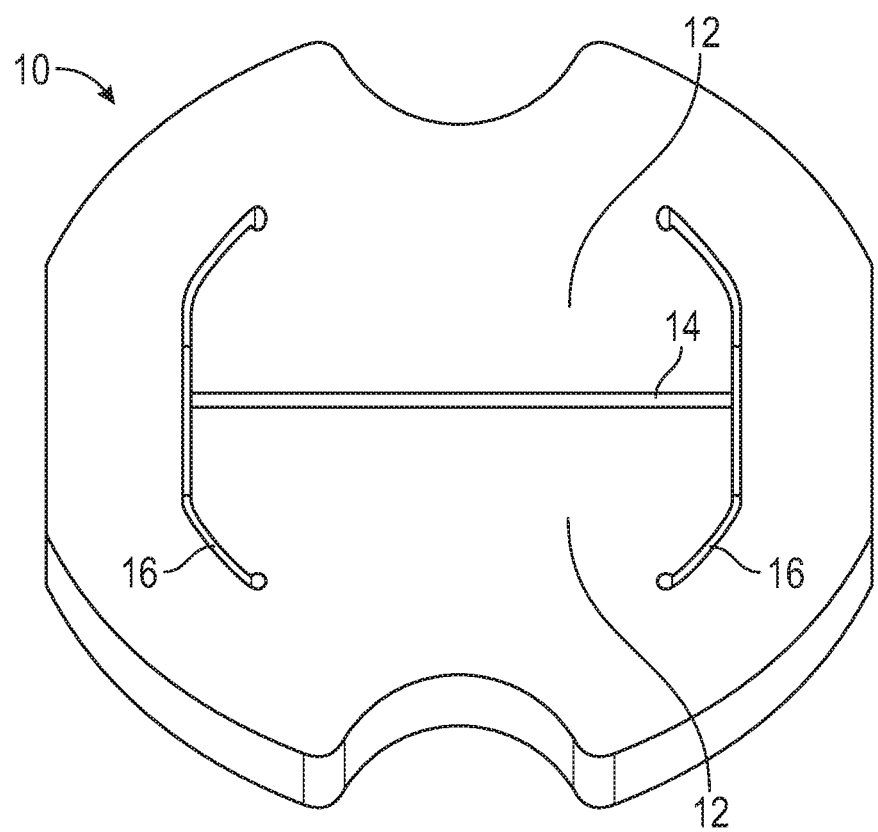
FIG. 1 is a perspective view of an exemplary suture clip.
Figure 2:
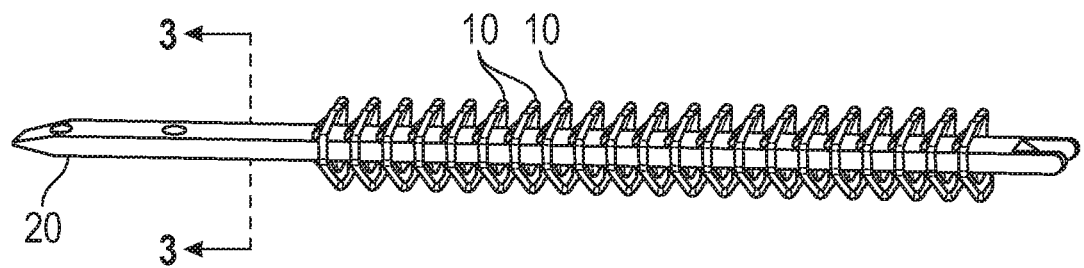
FIG. 2 shows several of the suture clips of FIG. 1 mounted on a rail of a deployment device.

Described herein are improved suture clips and related devices and methods for securing sutures with suture clips. FIG. 1 illustrates an exemplary suture clip 10 and FIG. 2 illustrates several of the clips 10 mounted on a rail, or mandrel, 20 of deployment device (see U.S. Patent Application Publication No. 2016/0183937 A1 for an exemplary deployment device using a similar clips-on-a-rail system). Additional information regarding procedures for which the disclosed suture clips and related delivery devices can be used, and other information regarding exemplary suture clips and suture clip delivery devices, are disclosed in the following references, the entire contents of which are expressly incorporated by reference herein: U.S. Pat. Nos. 6,626,930; 7,094,244; 7,083,628; and 7,381,210; and U.S. Patent Application Publication Nos. 2007/0005079 A1 and 2013/0165953 A1.

Figure 3:
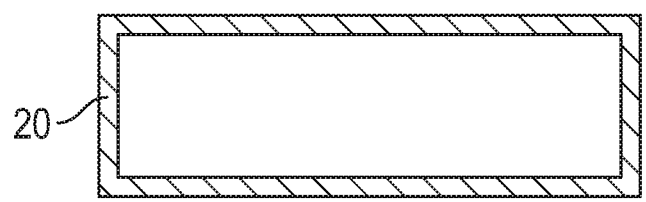
FIG. 3 is a cross-sectional view of the rail of FIG. 2.

FIG. 3 is an exemplary cross-sectional profile of the rail 20, showing a hollow central region that can receive sutures during the clip deployment process. A delivery device including the rail 20 can be loaded with suture clips and can be used to deploy loaded suture clips in succession onto one or more sutures, such as during implantation of a prosthetic device within the heart. The disclosed suture clips can be used to secure a single suture, or can be used to secure plural sutures or suture segments at the same time.

The clip 10 is generally disk shaped and includes an annular outer body and two opposing tabs 12 defined by slots 14 and 16 passing through the clip. The slot 14 is between the opposing edges of the two tabs 12, and is where sutures are engaged by the clip to secure the clip onto the sutures.

Any of the suture clips disclosed herein can comprise a resiliently deformable material that allows the opposing tabs to flex out of plane and apart from each other and open a space between the two tabs sufficient for the rail to pass through the clip between the tabs, as shown in FIGS. 2, 4, and 6-9. Any of the suture clips disclosed herein can be made from a variety of materials including, for example, nickel-titanium alloys, shape-memory alloys, stainless steel, titanium, various plastics, and other biologically-compatible materials. Exemplary suture clips can be formed from shape memory and/or pseudoelastic materials such as nitinol. In some embodiments, the suture clips can be formed from nitinol (e.g., with an alloy of nickel at about 54.5-57% by weight with titanium accounting for the balance except for residual amounts (less than about 0.05% each) of oxygen, carbon, and hydrogen) or another shape memory and/or pseudoelastic material, with the suture clips formed so that the clip assumes its closed position (e.g., the flat position shown in FIGS. 1 and 5) when in the austenite condition (e.g., when generally unstressed at body temperature). The nitinol can have an austenite finish temperature selected to match the particular application. For example, an austenite finish temperature of about −5 degrees to about +15 degrees Celsius may be selected.

Any of the suture clips disclosed herein can comprise more than one layer of material, with the layers stacked in the thickness dimension of the clip. Each layer can comprise a different material. The outer surfaces of the clips can include coatings in some embodiments. The thickness of the clip and/or the diameter of the clip can be any sizes, and can be selected based on the forces needed properly secure target sutures, the materials of the clips, the tissues through which the sutures pass, and/or other factors. Similarly, the spacing and length of the slot 114 between the opposing tabs 112 can be selected based on the size and material of the sutures to be secured and based on the number of sutures (1, 2, 3, etc.) to be secured by each clip. In some embodiments, the suture engagement slot 114 can be non-straight, such as comprising zig-zag portions or curved portions, which can help contain the sutures in the middle of the slot.

Figure 4:
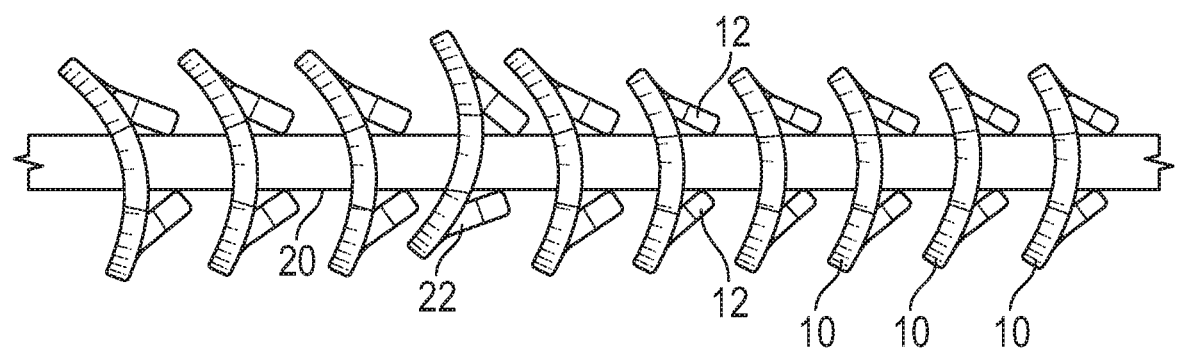
FIG. 4 illustrates how some suture clips can become undesirably misaligned on the rail.
Figure 6:
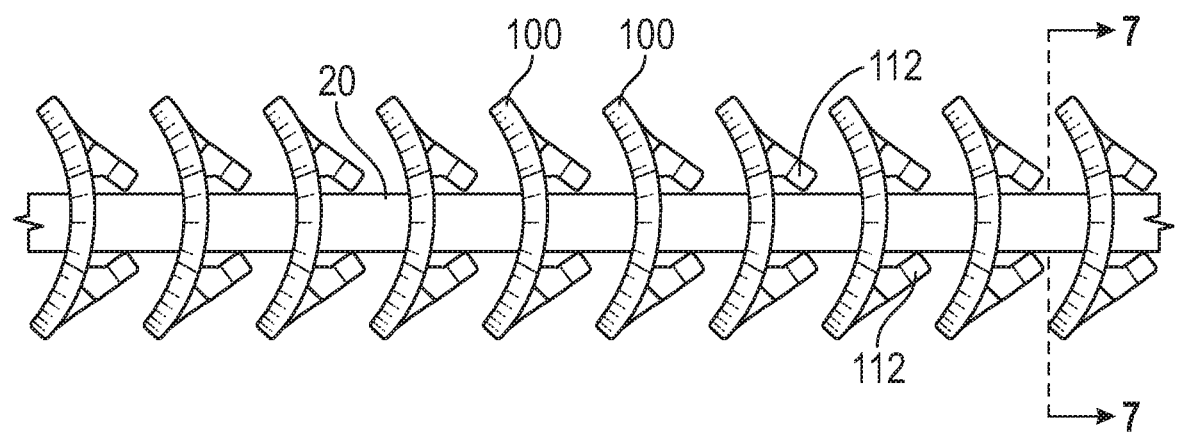
FIG. 6 shows several of the suture clips of FIG. 5 mounted on a rail in alignment.

A suture clip can be formed from material that will assume its martensite condition when subjected to sufficient stress, such as the stress applied to the clip's suture engagement tabs and annular outer body when the suture clip is mounted onto the rail, as shown in FIGS. 4 and 6. In such an embodiment, the rail applies stress to the engagement tabs, forcing the tabs to open wide enough to receive the rail through the opening between the tabs. The stressed material, including the bent material where the engagement tabs join the annular outer body, is forced into its martensite condition. When the stress is removed, such as when the rail slides out from within the distal-most clip during deployment, the material returns to its austenite condition so that the annular outer body and the engagement tabs assume their flat shape.

Figure 8:
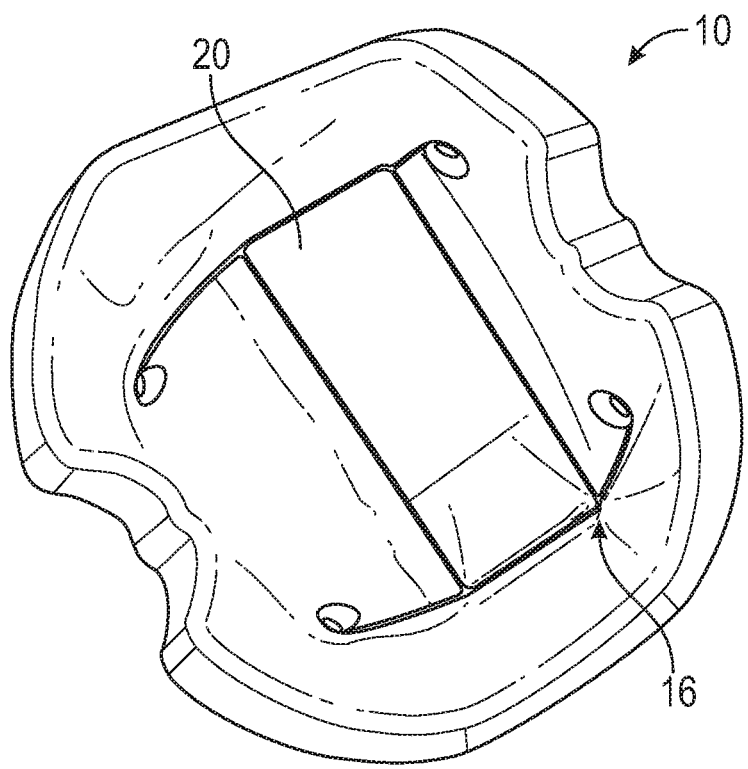
FIG. 8 is a perspective view of the suture clip of FIG. 1 mounted on a rail.

As illustrated in FIGS. 4 and 8, the clips 10 can sometimes become misaligned on the rail 20. For example, in FIG. 4 the clip 22 can shifted out of alignment relative to the rail and the other clips. For example, the smooth round shape of the slots 16 in the suture clips can allow the clips to rotate about the rail enough to become misaligned. This misalignment can be caused by a variety of causes, such as manual error during the loading of the clips onto the rail, impacts on the deployment device while the clips are loaded in the device, or uneven forces on the clip while the rail is slid through the clips during deployment. Whatever the cause, misaligned clips can fail to deploy properly onto sutures and/or can jam the deployment device. This can lead to increase time needed to complete a surgery and/or failure of the clip to secure a suture, which can increase the risk of harm to a patient.

Figure 5:
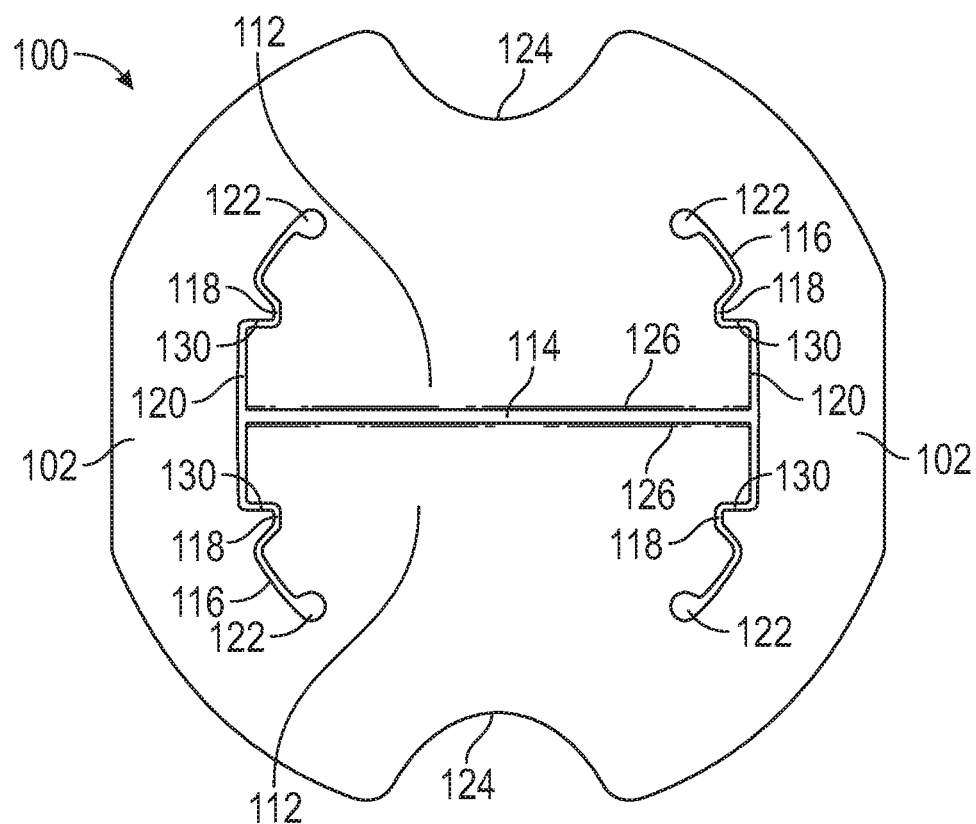
FIG. 5 is a plan view of another exemplary suture clip having pro-alignment features.

FIG. 5 is a plan view of an exemplary suture clip 100 that includes rail alignment features that help keep the suture clip properly oriented on a rail such as the rail 20, reducing the risk of the suture clips becoming misaligned and failing to deploy properly onto sutures. The clip 100 comprises an annular outer body 102 and two opposing suture engagement tabs 112 that extend inwardly from the outer body. The clip 100 has a suture engagement slot 114 defined between the tabs 112, and two lateral slots 116 positioned at either end of the slot 114 and separating the lateral sides of the tabs 112 from the outer body 102. Each of the lateral slots 116 include two steps 118, one on either side of the suture engagement slot 114. The steps 118 are portions of the slots 116 that extends radially inwardly into the tabs 112 a short distance. The slots 116 also include a generally straight portion 120 that extends between the two steps 118. The portion 120 can also be curved or partially curved. At the ends of the slots 116 are relief openings 122 that can reduce stress concentrations when the tabs 112 are bent while mounted on a rail. The clip 100 also includes opposing cutouts 124 that can help with gripping, loading, and/or manipulating the clips relative to a delivery device.

Figure 7:
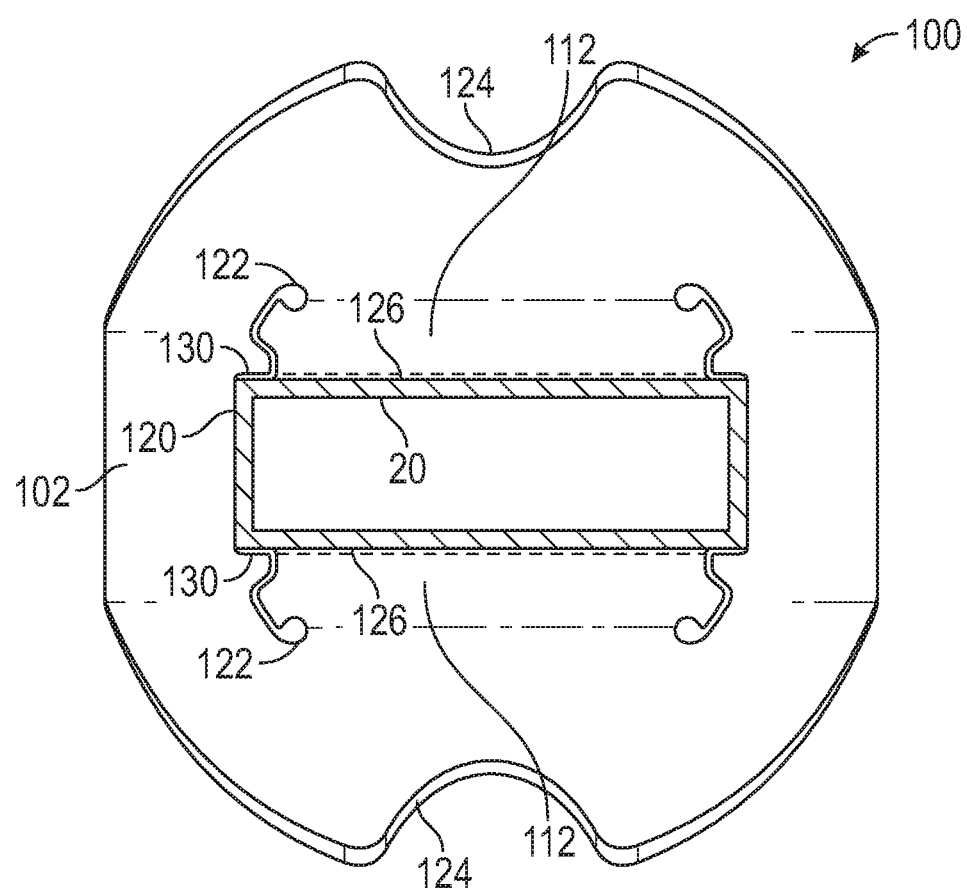
FIG. 7 is a cross-sectional view of the loaded rail of FIG. 6, taken at section 7-7.
Figure 9:
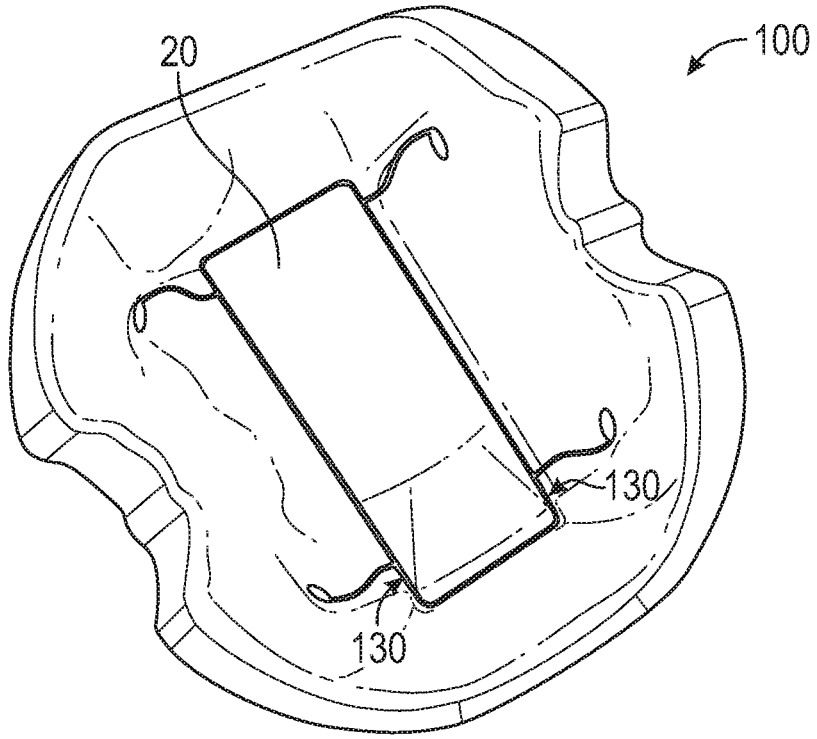
FIG. 9 is a perspective view of the suture clip of FIG. 5 mounted on a rail.

FIGS. 6, 7, and 9 illustrate the clip 100 mounted on a rail 20. When the clip 100 is mounted on a rail, the tabs flex out of plane relative to the outer body 102, with the flexure primarily occurring along hinge axes that extend between the relief openings 122, where the tabs joint the outer body and the width of the tab is narrowest. The outer body 102 can also flex a small amount in the opposite direction, as can be seen in FIG. 6, where the tabs 112 are extending to the right and the outer body is flexed slightly to the left.

When mounted on the rail 20, the clips 100 are retained via opposing clamping forces applied to the rail by the edges 126 of the tabs 112. These clamping forces are generated by the resilient deformation of the clips in the mounted configuration, as the tabs want to close back together toward the closed neutral position shown in FIG. 5. These same forces allow the tabs to clamp onto sutures positioned between the tabs 112 once deployed from the rail.

When mounted on the rail 20, the clips 100 are also held in alignment relative to the rail by surfaces 130 of the slot steps 118 and the walls of the slot portions 120. The surfaces 130 can contact the rail 20 and restrict the clips from tilting and shifting relative to the rail, preventing the misalignment such as the type shown in FIG. 4 with clip 22. There can be four of the surfaces 130, two on each of the lateral slots 116. The distance between each pair of opposing surfaces 130 can be selected to match the size of the rail 20. Similarly, the distance between the walls of the slot portions 120 can be selected to match the size of the rail. Together, the portions of the clip 120 and 130 can act to bracket the rail 20 and maintain the clip in proper alignment on the rail.

The features 118, 120, and 130 of the clips 100 can help the clips to be mounted on the rail in proper alignment during assembly; can help to prevent the clips from inadvertently shifting out of alignment or relaxing out of alignment after they are mounted on the rail; and/or can help to maintain the clips in proper alignment as the delivery device is actuated during use and as the clips 100 are caused to slide longitudinally down the length of the rail step-by-step, as each subsequent clip is deployed during a surgical procedure (see U.S. Patent Application Publication No. 2016/0183937 A1 for exemplary deployment devices and methods).

Figure 10:
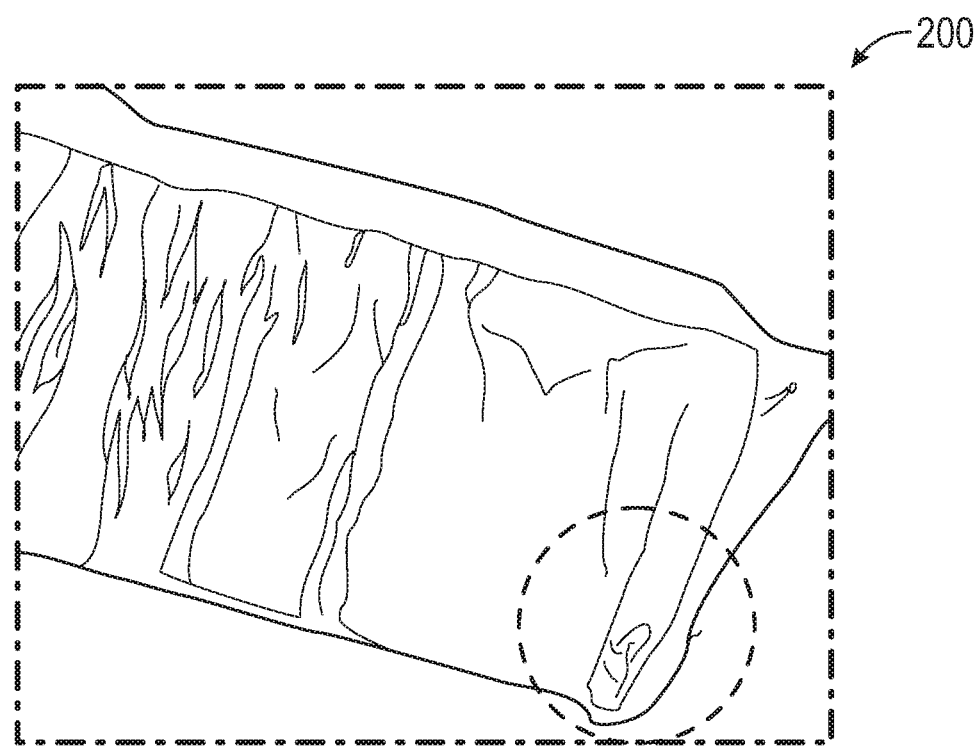
FIG. 10 illustrates how an exemplary suture clip tab having a sharp engagement edge can become damaged.
Figure 11:
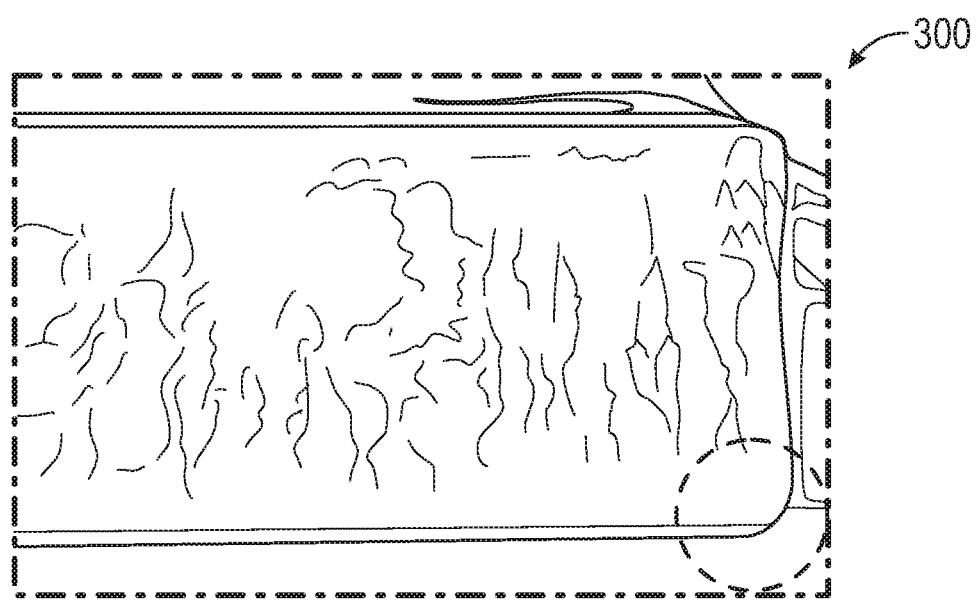
FIG. 11 illustrates an exemplary suture clip tab having a rounded engagement edge.

FIGS. 10 and 11 show detailed views on the suture engagement edges of two different suture clips. FIG. 10 shows an exemplary suture engagement edge 200 (such as can be present in suture clip 10) that is a sharp and angular.

Such a suture engagement edge can be problematic, as the sharp edge can cut or damage a suture and the sharp edge can more easily become plastically deformed and damaged, leading to particular matter coming loose from the suture clip and harming the patient. By contrast, FIG. 11 shows an exemplary suture engagement edge 300 (such as can be present in suture clip 100) that is rounded and smooth, reducing/eliminating the risk of the edge becoming damaged, sutures being damaged by the edges, loose particulates harming patients, etc. The rounded edges 126 of the clip 100 also protect against damage when the edges 126 are contacting and sliding along the side of the rail 20, as in FIG. 6.

The suture clip 100, for example, can include four suture engagement edges, two on each tab 112. Each tab 112 can have one such edge on each side of the clip, such that the clips are symmetrical about a plane slicing through the middle of the thickness of the clip. The clips can also be symmetrical about planes cutting through the width of the clip along the slot 114 and cutting through the orthogonal width between the cutouts 124. In this way, the clips can be used in any orientation (e.g., flipped 180 degrees and/or rotated 180 degrees) so long as the clip is oriented relative to the rail 20 as shown in FIG. 7. This prevents accidental mis-loading of the clips.

In some embodiments of the disclosed technology, the rail of the deployment device and/or the suture clips can include a coating or lubricant that reduces friction between the suture clips and the rail, which can make it easier to load and deploy the clips on and off of the rail, and can reduce scraping and particulate generation as the clips move over the rail. The rail and/or the suture clips can include a coating of a solid material and/or a viscous lubricant, including dry and wet lubricants. Exemplary coating/lubricant materials can include PTFE (e.g., DURAGLIDE dry PTFE lubricant, MicroCare Medical, New Britain, Conn.) or other dry lubricants such as, graphite, and molybdenum disulfide; grease and other petroleum-based lubricants; polymer based lubricants, for example, silicone lubricants; metallic materials such as gold plating, and other materials applied via physical vapor deposition or chemical vapor deposition (e.g., CVD diamond or diamond-like films); and combinations thereof.

For purposes of this description, certain aspects, advantages, and novel features of the embodiments of this disclosure are described herein. The disclosed suture clips, devices, methods, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, characteristics, materials, compounds, integers, or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods and devices can be used in conjunction with other methods and devices.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad as the following claims. We therefore claim all that comes within the scope of the following claims.

What is claimed is:

1. A suture clip deployment system comprising:
  a rail having a rectangular cross-sectional shape; and
  a suture clip mounted on the rail, the suture clip comprising:
    a generally disk-shaped body having an annular outer body positioned around the rail;
    a first tab extending radially inwardly from a first side of the annular outer body and contacting a first side of the rail;
    a second tab extending radially inwardly from a second, opposing side of the annular outer body and contacting a second side of the rail opposite the first side of the rail; and
    a first slot and a second slot passing through a thickness of the suture clip and separating the annular outer body from lateral sides of the first tab and second tab such that the first and second tabs can deform to receive the rail between them;
  wherein the first and second slots comprise stepped portions that align the suture clip relative to the rectangular cross-sectional shape of the rail; wherein the first slot comprises a straight portion that extends between two of the stepped portions and is positions adjacent third side of the rail, and wherein the second slot comprises a straight portion that extends between two of the stepped portions and is positioned adjacent fourth side of the rail opposite the third side of the rail.

2. The system of claim 1, wherein the stepped portions comprise steps that extend inwardly from the annular outer body and contact the first and second sides of the rail and thereby restrict the suture clip from shifting perpendicular to a longitudinal axis of the rail.

3. The system of claim 1, wherein the first and second tabs comprise opposing rail engagement surfaces, and the rail engagement surfaces comprise rounded edges.

4. The system of claim 1, wherein the rail comprises a coating or lubricant that reduces friction between the rail and the suture clip.

5. The system of claim 1, wherein the stepped portions define indentations in lateral sides of the first and second tabs.

6. The system of claim 1, wherein the stepped portions are spaced apart by a distance that corresponds to a width dimension of the rail.

7. The system of claim 1, wherein the first and second tabs are resiliently deformed such that the suture engagement slot allows the rail to extend between the first and second tabs.

8. The system of claim 7, wherein the first and second slots terminate in enlarged circular portions located where the first and second tabs join with the annular outer body, such that the enlarged circular portions reduce stress concentrations caused by the first and second tabs being resiliently deformed relative to the annular outer body along hinge axes extending between the enlarged circular portions.

9. The system of claim 1, wherein the suture clip is the first suture clip, and the system further comprises a second suture clip mounted on the rail, the second suture clip being identical to the first suture clip and spaced apart from the first suture clip along a length of the rail.

* * * * *